(12) United States Patent
Fain et al.

(10) Patent No.: US 7,187,972 B1
(45) Date of Patent: Mar. 6, 2007

(54) BI-VENTRICULAR PACING IN THE FACE OF RAPIDLY CONDUCTING ATRIAL TACHYARRHYTHMIA

(75) Inventors: Eric Fain, Menlo Park, CA (US); Eliot Ostrow, Sunnyvale, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 331 days.

(21) Appl. No.: 10/993,966

(22) Filed: Nov. 18, 2004

(51) Int. Cl.
*A61N 1/368* (2006.01)
(52) U.S. Cl. .................................................. 607/14
(58) Field of Classification Search .............. 607/4, 607/5, 14, 15
See application file for complete search history.

(56) References Cited

U.S. PATENT DOCUMENTS

| | | | |
|---|---|---|---|
| 4,944,298 A | 7/1990 | Sholder | 128/419 PG |
| 5,133,350 A | 7/1992 | Duffin | 128/419 PG |
| 5,144,949 A | 9/1992 | Olson | 128/419 PG |
| 5,292,340 A | 3/1994 | Crosby et al. | 607/17 |
| 5,549,649 A | 8/1996 | Florio et al. | 607/15 |
| 6,081,747 A | 6/2000 | Levine et al. | 607/9 |
| 6,285,907 B1 | 9/2001 | Kramer et al. | 607/9 |
| 6,411,848 B2 | 6/2002 | Kramer et al. | 607/9 |
| 6,477,420 B1 | 11/2002 | Struble et al. | 607/14 |
| 6,501,988 B2 | 12/2002 | Kramer et al. | 607/9 |
| 7,142,918 B2 * | 11/2006 | Stahmann et al. | 607/15 |
| 2001/0016759 A1 | 8/2001 | Kramer et al. | 607/9 |
| 2002/0082648 A1 | 6/2002 | Kramer et al. | 607/9 |
| 2002/0082660 A1 | 6/2002 | Stahmann et al. | 607/14 |
| 2003/0069610 A1 | 4/2003 | Kramer et al. | 607/25 |
| 2005/0187585 A1 * | 8/2005 | Mussing et al. | 607/9 |

FOREIGN PATENT DOCUMENTS

| | | |
|---|---|---|
| WO | WO 00/71202 A1 | 11/2000 |
| WO | WO 02/051496 A2 | 7/2002 |
| WO | WO 02/051496 A3 | 7/2002 |

\* cited by examiner

*Primary Examiner*—Kennedy Schaetzle
(74) *Attorney, Agent, or Firm*—Steven M. Mitchell

(57) ABSTRACT

Methods and devices (e.g., pacemakers or ICDs with pacemaker functions) are provided for maintaining a high percentage of bi-ventricular pacing after a pacemaker switches from an atrial tracking bi-ventricular pacing mode to a non-atrial tracking bi-ventricular pacing mode, wherein the ventricles are paced in accordance with a mode switch base rate (MSBR) during the non-atrial tracking ventricular pacing mode. Monitoring is performed to determine whether or not pacing in according with the MSBR satisfies a minimum acceptable pacing criterion (MAPC). The MSBR is increased and pacing is performed in accordance with the increased MSBR, when the MAPC is not satisfied. The MSBR is decreased (e.g., periodically) and pacing is performed in accordance with the decreased MSBR when the MAPC is satisfied.

38 Claims, 3 Drawing Sheets

BI-VENTRICULAR PACING IN THE FACE OF RAPIDLY CONDUCTING ATRIAL TACHYARRHYTHMIA

FIELD OF THE INVENTION

The present invention relates generally to programmable implantable pacemakers, and implantable cardioverter-defibrillators (ICDs) with pacemaker functions, and particularly those devices that stimulate the atrium and both the left and right ventricles, and that are capable of switching from an atrial tracking bi-ventricular pacing mode to a non-atrial tracking bi-ventricular pacing mode in response to an occurrence of an atrial arrhythmia.

BACKGROUND

Essentially, the heart is a pump which pumps blood throughout the body. It consists of four chambers, including a left atrium, a right atrium, a left ventricle and a right ventricle. In order for the heart to efficiently perform its function as a pump, the atrial muscles and ventricular muscles should contract in a proper sequence and in a timed relationship.

In a given cardiac cycle (corresponding to one "beat" of the heart), the two atria contract, forcing the blood therein into the ventricles. A short time later, the two ventricles contract, forcing the blood therein to the lungs (from the right ventricle) or through the body (from the left ventricle). Meanwhile, blood from the body fills the right atrium and blood from the lungs fills the left atrium, waiting for the next cycle to begin. A typical healthy adult heart may beat at a rate of 60–70 beats per minute (bpm) while at rest, and may increase its rate to 140–180 bpm when the adult is engaging in strenuous physical exercise, or undergoing other physiologic stress.

The healthy heart controls its rhythm from its sinoatrial (SA) node, located in the upper portion of the right atrium. The SA node generates an electrical impulse at a rate commonly referred to as the "sinus" rate. This impulse is delivered to the atrial tissue when the atria are to contract and, after a suitable delay, propagates to the ventricular tissue when the ventricles are to contract.

When the atria contract, a detectable electrical signal referred to as a P-wave is generated. When the ventricles contract, a detectable electrical signal referred to as the QRS complex (also referred to simply an "R-wave") is generated, as a result of the depolarization of the ventricles. The R-wave is much larger than the P-wave, principally because the ventricular muscle tissue is much more massive than the atrial muscle tissue. The atrial muscle tissue need only produce a contraction sufficient to move the blood a very short distance—from the respective atrium to its corresponding ventricle. The ventricular muscle tissue, on the other hand, must produce a contraction sufficient to push the blood over a long distance (e.g., through the complete circulatory system of the entire body).

It is the function of a pacemaker to provide electrical stimulation pulses to the appropriate chamber(s) of the heart (atria and/or ventricles) in the event the heart is unable to beat on its own (e.g., in the event either the SA node fails to generate its own natural stimulation pulses at an appropriate sinus rate, or in the event such natural stimulation pulses do not effectively propagate to the appropriate cardiac tissue). Most modern pacemakers accomplish this function by operating in a "demand" mode where stimulation pulses from the pacemaker are provided to the heart only when it is not beating on its own, as sensed by monitoring the appropriate chamber of the heart for the occurrence of a P-wave or an R-wave. If a P-wave or an R-wave is not sensed within a prescribed period of time (which period of time is often referred to as the "escape interval"), then a stimulation pulse is generated at the conclusion of this prescribed period of time and delivered to the appropriate heart chamber via a pacemaker lead.

Modern programmable pacemakers are generally of two types: (1) single chamber pacemakers, and (2) dual-chamber pacemakers. In a single chamber pacemaker, the pacemaker provides stimulation pulses to, and senses cardiac activity within, a single-chamber of the heart (e.g., either the right ventricle or the right atrium). In a dual-chamber pacemaker, the pacemaker provides stimulation pulses to, and senses cardiac activity within, two chambers of the heart (e.g., both the right atrium and the right ventricle). The left atrium and left ventricle can also be paced, provided that suitable electrical contacts are made therewith.

During atrial tracking bi-ventricular pacing, pacing or sensing occurs in the atria, then (after a programmed time period) pacing occurs in the ventricles. In this manner, the bi-ventricular pacing tracks the rate of the atria (where the heart beat starts). Unfortunately, in some instances, a given patient may develop fast atrial rhythms which result from a pathologic arrhythmia such as a pathologic tachycardia, fibrillation or flutter. In these cases, non-mode-switching dual-chamber pacemakers can pace the ventricles in response to the sensed atrial arrhythmia only up to the programmed maximum tracking rate (MTR). This, however, will allow the ventricles to intrinsically beat in a deleterious non-synchronous manner when the intrinsic rate is greater than the MTR.

Standard modern dual-chamber pacemakers now prevent undesirable tracking of certain atrial arrhythmias by automatically switching the pacemaker's mode of operation from an atrial tracking pacing mode to a non-atrial tracking pacing mode. For example, U.S. Pat. No. 4,722,341 to Hedberg et al., teaches an atrium-controlled pacemaker, where the pacemaker temporarily switches from an atrial tracking mode to a non-atrial tracking mode for a fixed number of stimulation pulses if the sensed atrial activity indicates an atrial arrhythmia may be developing. This behavior has carried over to bi-ventricular devices, even though it may be less appropriate under those circumstances During atrial fibrillation (AF), a standard modern dual-chamber bradycardia pacemaker switches to a non-atrial tracking mode to prevent rapid, irregular ventricular pacing. However, when the intrinsic ventricular response to the AF is faster than the pacing rate, pacing is inhibited. While this is an appropriate response for a standard demand type bradycardia pacemaker, which is designed to prevent the patient's heart rate from falling below a certain minimum limit, it is not appropriate for newer devices targeted to patients with heart failure (HF). For HF patients, whose pacemakers pace both ventricles (referred to as bi-ventricular pacing or BiV pacing), the benefit of the device is best realized with continuous, or nearly continuous, bi-ventricular pacing. Thus, during rapidly conducted AF, a different response is needed to maximize bi-ventricular pacing.

More specifically, when a patient goes into AF, the typical response of a BiV pacemaker (also referred to herein simply as "the device") is to switch from an atrial tracking mode to a non-atrial tracking mode to prevent the fast, irregular tracking of the atrial fibrillation by the device. When the device mode switches, it typically goes to either a fixed BiV pacing rate, or to an adjustable BiV pacing rate that provides rate response based on the patient's level of activity or other available indicators of the patient's physiologic need. For the sake of consistency, the BiV pacing rate during mode switch (i.e., during a non-atrial tracking bi-ventricular pacing mode) will be hereafter referred to as the "mode switch base rate" or simply as "MSBR". If the patient's intrinsic rate is above the MSBR, the pacemaker's output is inhibited. For HF patients with devices that deliver BiV pacing, such inhibition of pacing negates the benefit of cardiac resynchronization that BiV pacing is intended to confer. Specifically, if the patient remains in AF for long periods of time, this can have a deleterious effect on the patient's clinical condition. It would be advantageous if such deleterious effects can be reduced and preferably minimized.

SUMMARY

Embodiments of the present invention are directed to methods and devices (i.e., pacemakers) that maintain a high percentage of bi-ventricular pacing after a pacemaker switches from an atrial tracking bi-ventricular pacing mode to a non-atrial tracking bi-ventricular pacing mode, wherein the ventricles are paced in accordance with a mode switch base rate (MSBR) during the non-atrial tracking bi-ventricular pacing mode. Such a switch from an atrial tracking bi-ventricular pacing mode to a non-atrial tracking bi-ventricular pacing mode may occur, e.g., in response to detection of an atrial tachyarrhythmia, such as atrial fibrillation (AF).

In accordance with embodiments of the present invention, when a pacemaker switches from an atrial tracking bi-ventricular pacing mode to a non-atrial tracking bi-ventricular pacing mode in response to an atrial fibrillation (or other atrial tachyarrhythmia) being detected, the device paces in accordance with the MSBR, which can be an initial rate or a rate that has been previously specified by an algorithm of the present invention. When in mode switch (i.e., in a non-atrial tracking bi-ventricular pacing mode), the pacemaker repeatedly determines whether a minimum acceptable pacing criterion (MAPC) is being satisfied (i.e., met or exceeded). If the frequency of bi-ventricular pacing does not satisfy the MAPC, then the pacemaker will gradually increase the MSBR until the MAPC is satisfied or a maximum MSBR is reached (or the pacemaker is no longer in mode switch). When the frequency of bi-ventricular pacing satisfies the MAPC, then the pacemaker will periodically (e.g., after a time based period or an elapsed interval criterion) decrease the MSBR until either the minimum MSBR is reached or the MAPC is no longer satisfied (or the pacemaker is no longer in mode switch). If the MSBR is decreased to the point where the MAPC is no longer satisfied, the pacemaker will then gradually increase the MSBR until the MAPC is again satisfied or a maximum MSBR is reached (or the pacemaker is no longer in mode switch). In this manner, the MSBR is incrementally increased and decreased in an attempt to maintain the minimum BiV pacing rate necessary to meet the MAPC.

While not limited thereto, embodiments of the present invention are especially useful for HF treatment and other cardiac resynchronization therapy (CRT), where a pacemaker is ideally trying to pace the two ventricles all of the time, so as to not allow the ventricles to depolarize naturally, because the intrinsic depolarizations of the right and left ventricles are not properly synchronized.

Other features and advantages of the invention will appear from the following description in which the preferred embodiments have been set forth in detail, in conjunction with the accompanying drawings and claims.

DETAILED DESCRIPTION

Exemplary Pacing Device

Figure 1:
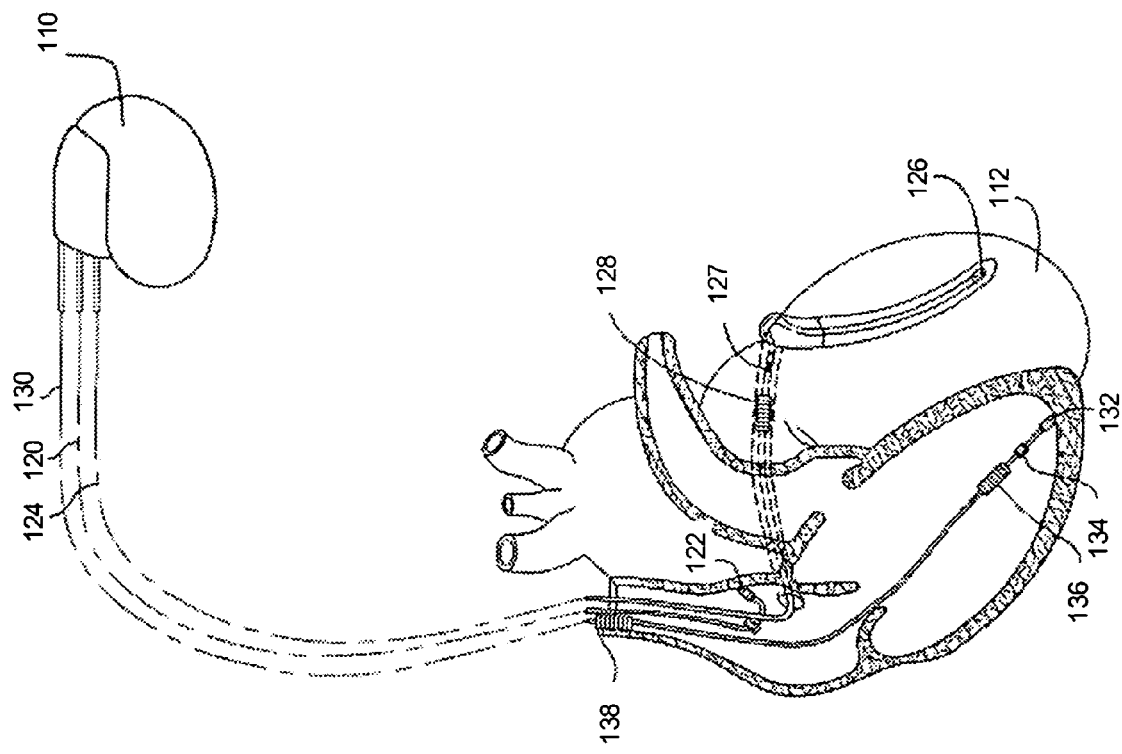
FIG. 1 illustrates an exemplary multi-chamber implantable stimulation device in electrical communication with a patient's heart by way of three leads, which are suitable for delivering multi-chamber pacing, as well as shock therapy.

Before describing specific embodiments of the present invention, it is useful to first describe an exemplary multi-chamber pacing device. Referring to FIG. 1, an exemplary implantable pacemaker 110 (also referred to as a pacing device, a pacing apparatus, a stimulation device, or simply a device) is in electrical communication with a patient's heart 112 by way of three leads, 120, 124 and 130, suitable for delivering multi-chamber stimulation. While not necessary to perform embodiments of the present invention, the exemplary device 110 is also capable of delivering shock therapy.

To sense atrial cardiac signals and to provide right atrial chamber stimulation therapy, the stimulation device 110 is coupled to an implantable right atrial lead 120 having at least an atrial tip electrode 122, which typically is implanted in the patient's right atrial appendage. To sense left atrial and ventricular cardiac signals and to provide left-chamber pacing therapy, the stimulation device 110 is coupled to a "coronary sinus" lead 124 designed for placement in the "coronary sinus region" via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 124 is designed to receive left atrial and ventricular cardiac signals and to deliver left atrial and ventricular pacing therapy using at least a left ventricular tip electrode 126, left atrial pacing therapy using at least a left atrial ring electrode 127, and shocking therapy using at least a left atrial coil electrode 128. The present invention may of course be practiced with a coronary sinus lead that does not include left atrial sensing, pacing or shocking electrodes.

The stimulation device 110 is also shown in electrical communication with the patient's heart 112 by way of an implantable right ventricular lead 130 having, in this embodiment, a right ventricular tip electrode 132, a right ventricular ring electrode 134, a right ventricular (RV) coil electrode 136, and an SVC coil electrode 138. Typically, the right ventricular lead 130 is transvenously inserted into the heart 112 so as to place the right ventricular tip electrode 132 in the right ventricular apex so that the RV coil electrode 136 will be positioned in the right ventricle and the SVC coil electrode 138 will be positioned in the superior vena cava. Accordingly, the right ventricular lead 130 is capable of receiving cardiac signals and delivering stimulation in the form of pacing and shock therapy to the right ventricle. It will be understood by those skilled in the art that other lead and electrode configurations such as epicardial leads and electrodes may be used in practicing the invention.

Figure 2:
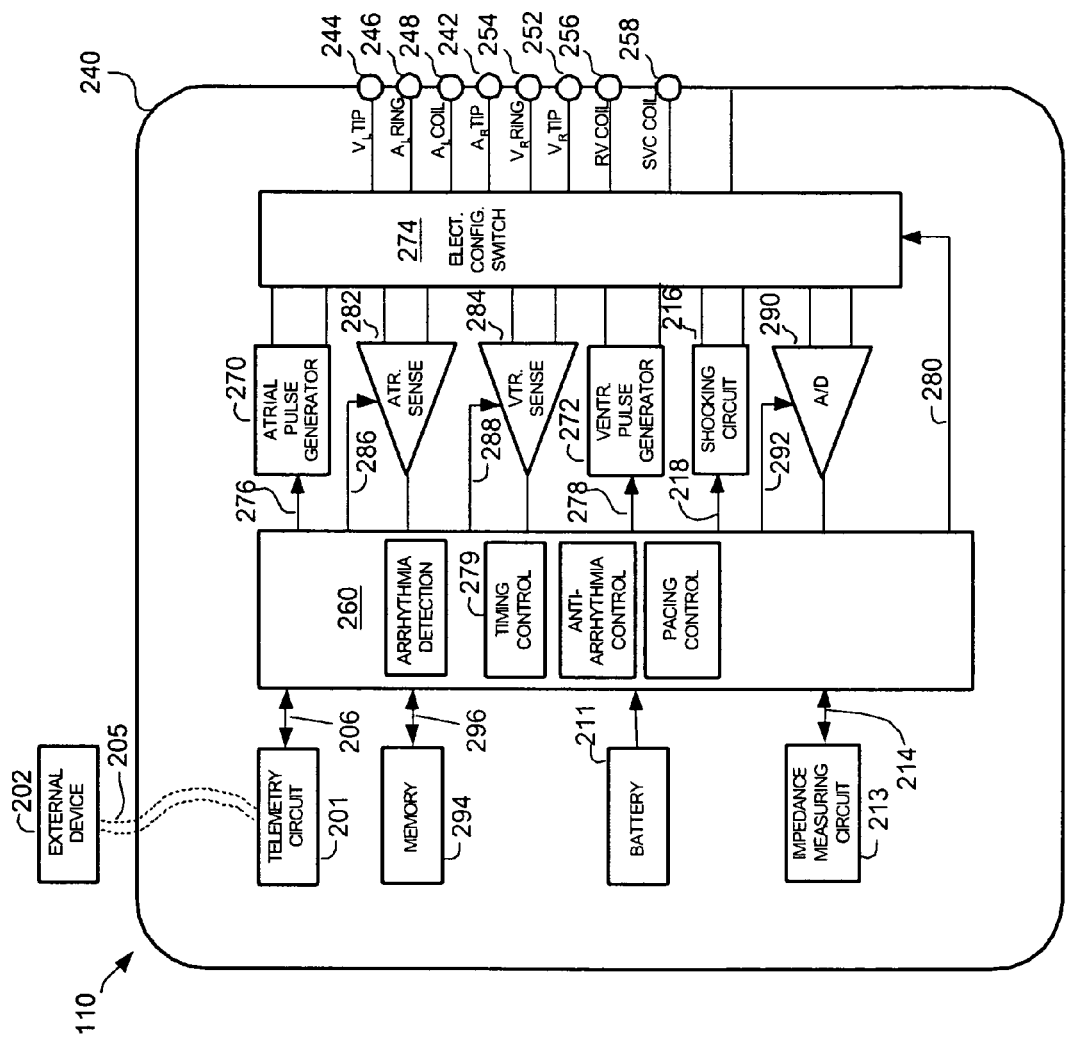
FIG. 2 is a simplified block diagram of the multi-chamber implantable stimulation device of FIG. 1.

As illustrated in FIG. 2, a simplified block diagram is shown of the multi-chamber implantable pacing device 110, which is capable of treating both fast and slow arrhythmias with stimulation therapy, including pacing, cardioversion and defibrillation stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with pacing, cardioversion and defibrillation stimulation.

The housing 240 for the pacing device 110, shown schematically in FIG. 2, is often referred to as the "can", "case" or "case electrode" and may be programmably selected to act as the return electrode for all "unipolar" modes. The housing 240 may further be used as a return electrode alone or in combination with one or more of the coil electrodes, 128, 136 and 138, for shocking purposes. The housing 240 further includes a connector (not shown) having a plurality of terminals, 242, 244, 246, 248, 252, 254, 256, and 258 (shown schematically and, for convenience, the names of the electrodes to which they are connected are shown next to the terminals). As such, to achieve right atrial sensing and pacing, the connector includes at least a right atrial tip terminal ($A_R$ TIP) 242 adapted for connection to the atrial tip electrode 122.

To achieve left atrial and ventricular sensing, pacing and shocking, the connector includes at least a left ventricular tip terminal ($V_L$ TIP) 244, a left atrial ring terminal ($A_L$ RING) 246, and a left atrial shocking terminal ($A_L$ COIL) 148, which are adapted for connection to the left ventricular ring electrode 126, the left atrial tip electrode 127, and the left atrial coil electrode 128, respectively.

To support right ventricle sensing, pacing and shocking, the connector further includes a right ventricular tip terminal ($V_R$ TIP) 252, a right ventricular ring terminal ($V_R$ RING) 254, a right ventricular shocking terminal ($R_V$ COIL) 256, and an SVC shocking terminal (SVC COIL) 258, which are adapted for connection to the right ventricular tip electrode 132, right ventricular ring electrode 134, the RV coil electrode 136, and the SVC coil electrode 138, respectively.

At the core of the pacing device 110 is a programmable microcontroller 260 which controls the various types and modes of stimulation therapy. As is well known in the art, the microcontroller 260 typically includes a microprocessor, or equivalent control circuitry, designed specifically for controlling the delivery of stimulation therapy and can further include RAM or ROM memory, logic and timing circuitry, state machine circuitry, and I/O circuitry. Typically, the microcontroller 260 includes the ability to process or monitor input signals (data) as controlled by a program code stored in a designated block of memory. The details of the design of the microcontroller 260 are not critical to the present invention. Rather, any suitable microcontroller 260 can be used to carry out the functions described herein. The use of microprocessor-based control circuits for performing timing and data analysis functions are well known in the art. In specific embodiments of the present invention, the microcontroller 260 performs some or all of the steps associated with arrhythmia detection, selecting an appropriate anti-arrhythmia therapy, performing a mode switch from an atrial tracking ventricular pacing mode to a non-atrial tracking ventricular pacing mode, as well as maintaining a high percentage of pacing during mode switch.

Representative types of control circuitry that may be used with the invention include the microprocessor-based control system of U.S. Pat. No. 4,940,052 (Mann et. al.) and the state-machines of U.S. Pat. No. 4,712,555 (Sholder) and U.S. Pat. No. 4,944,298 (Sholder). For a more detailed description of the various timing intervals used within the pacing device and their inter-relationship, see U.S. Pat. No. 4,788,980 (Mann et. al.). The '052, '555, '298 and '980 patents are incorporated herein by reference.

An atrial pulse generator 270 and a ventricular pulse generator 272 generate pacing stimulation pulses for delivery by the right atrial lead 120, the right ventricular lead 130, and/or the coronary sinus lead 124 via an electrode configuration switch 274. It is understood that in order to provide stimulation therapy in each of the four chambers of the heart, the atrial and ventricular pulse generators, 270 and 272, may include dedicated, independent pulse generators, multiplexed pulse generators, or shared pulse generators. The pulse generators, 270 and 272, are controlled by the microcontroller 260 via appropriate control signals, 276 and 278, respectively, to trigger or inhibit the stimulation pulses.

The microcontroller 260 further includes timing control circuitry 279 which is used to control pacing parameters (e.g., the timing of stimulation pulses) as well as to keep track of the timing of refractory periods, noise detection windows, evoked response windows, alert intervals, marker channel timing, etc., which is well known in the art. Examples of pacing parameters include, but are not limited to, atrio-ventricular delay, interventricular delay and interatrial delay.

The switch bank 274 includes a plurality of switches for connecting the desired electrodes to the appropriate I/O circuits, thereby providing complete electrode programmability. Accordingly, the switch 274, in response to a control signal 280 from the microcontroller 260, determines the polarity of the stimulation pulses (e.g., unipolar, bipolar, etc.) by selectively closing the appropriate combination of switches (not shown) as is known in the art.

Atrial sensing circuits 282 and ventricular sensing circuits 284 may also be selectively coupled to the right atrial lead 120, coronary sinus lead 124, and the right ventricular lead 130, through the switch 274 for detecting the presence of cardiac activity in each of the four chambers of the heart. Accordingly, the atrial (ATR. SENSE) and ventricular (VTR. SENSE) sensing circuits, 282 and 284, may include dedicated sense amplifiers, multiplexed amplifiers, or shared amplifiers. The switch 274 determines the "sensing polarity" of the cardiac signal by selectively closing the appropriate switches, as is also known in the art. In this way, the clinician may program the sensing polarity independent of the stimulation polarity.

Each sensing circuit, 282 and 284, preferably employs one or more low power, precision amplifiers with programmable gain and/or automatic gain control, bandpass filtering, and a threshold detection circuit, as known in the art, to selectively sense the cardiac signal of interest. The automatic gain control enables the device 110 to deal effectively with the difficult problem of sensing the low amplitude signal characteristics of atrial or ventricular fibrillation. Such sensing circuits, 282 and 284, can be used to determine cardiac performance values used in the present invention. Alternatively, an automatic sensitivity control circuit may be used to effectively deal with signals of varying amplitude.

The outputs of the atrial and ventricular sensing circuits, 282 and 284, are connected to the microcontroller 260 which, in turn, are able to trigger or inhibit the atrial and ventricular pulse generators, 270 and 272, respectively, in a demand fashion in response to the absence or presence of cardiac activity, in the appropriate chambers of the heart. The sensing circuits, 282 and 284, in turn, receive control signals over signal lines, 286 and 288, from the microcontroller 260 for purposes of measuring cardiac performance at appropriate times, and for controlling the gain, threshold, polarization charge removal circuitry (not shown), and timing of any blocking circuitry (not shown) coupled to the inputs of the sensing circuits, 282 and 286.

For arrhythmia detection, the device 110 utilizes the atrial and ventricular sensing circuits, 282 and 284, to sense cardiac signals to determine whether a rhythm is physiologic or pathologic. The timing intervals between sensed events (e.g., P-waves, R-waves, and depolarization signals associated with fibrillation) are then classified by the microcontroller 260 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to assist with determining the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 290. The data acquisition system 290 is configured to acquire intracardiac electrogram signals, convert the raw analog data into a digital signal, and store the digital signals for later processing and/or telemetric transmission to an external device 202. The data acquisition system 290 is coupled to the right atrial lead 120, the coronary sinus lead 124, and the right ventricular lead 130 through the switch 274 to sample cardiac signals across any pair of desired electrodes.

Advantageously, the data acquisition system 290 can be coupled to the microcontroller 260, or other detection circuitry, for detecting an evoked response from the heart 212 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 260 detects a depolarization signal during a window following a stimulation pulse, the presence of which indicates that capture has occurred. The microcontroller 260 enables capture detection by triggering the ventricular pulse generator 272 to generate a stimulation pulse, starting a capture detection window using the timing control circuitry 279 within the microcontroller 260, and enabling the data acquisition system 290 via control signal 292 to sample the cardiac signal that falls in the capture detection window and, based on the amplitude, determines if capture has occurred.

The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et. al.); and U.S. Pat. No. 5,350,410 (Mann et. al.), which patents are hereby incorporated herein by reference. The type of capture detection system used is not critical to the present invention.

The microcontroller 260 is further coupled to a memory 294 by a suitable data/address bus 296, wherein the programmable operating parameters used by the microcontroller 260 are stored and modified, as required, in order to customize the operation of the pacing device 110 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 212 within each respective tier of therapy. In accordance with embodiments of the present invention, other operating parameters include a mode switch base rate (MSBR) and a minimum acceptable pacing criterion (MAPC), each of which is discussed in more detail below.

Advantageously, the operating parameters of the implantable device 110 may be non-invasively programmed into the memory 294 through a telemetry circuit 201 in telemetric communication with the external device 202, such as a programmer, transtelephonic transceiver, or a diagnostic system analyzer. The telemetry circuit 201 can be activated by the microcontroller 260 by a control signal 206. The telemetry circuit 201 advantageously allows intracardiac electrograms and status information relating to the operation of the device 110 (as contained in the microcontroller 260 or memory 294) to be sent to an external device 202 through an established communication link 204.

For examples of such devices, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. Pat. No. 6,275,734 entitled "Efficient Generation of Sensing Signals in an Implantable Medical Device such as a Pacemaker or ICD" (McClure et al.), which patents are hereby incorporated herein by reference.

The pacing device 110 additionally includes a battery 211 which provides operating power to all of the circuits shown in FIG. 2. If the pacing device 110 also employs shocking therapy, the battery 211 should be capable of operating at low current drains for long periods of time, and then be capable of providing high-current pulses (for capacitor charging) when the patient requires a shock pulse. The battery 211 should also have a predictable discharge characteristic so that elective replacement time can be detected.

The pacing device 110 can also include a magnet detection circuitry (not shown), coupled to the microcontroller 260. It is the purpose of the magnet detection circuitry to detect when a magnet is placed over the pacing device 110, which magnet may be used by a clinician to perform various test functions of the pacing device 110 and/or to signal the microcontroller 260 that the external programmer 202 is in place to receive or transmit data to the microcontroller 260 through the telemetry circuits 201.

As further shown in FIG. 2, the device 110 is also shown as having an impedance measuring circuit 213 which is enabled by the microcontroller 260 via a control signal 214. The known uses for an impedance measuring circuit 213 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds and heart failure condition; detecting when the device has been implanted; measuring stroke volume; and detecting the opening of heart valves, etc. The impedance measuring circuit 213 is advantageously coupled to the switch 274 so that any desired electrode may be used. The impedance measuring circuit 213 is not critical to the present invention and is shown only for completeness.

In the case where the pacing device 110 is also intended to operate as an implantable cardioverter/defibrillator (ICD)

device, it must detect the occurrence of an arrhythmia, and automatically apply an appropriate electrical shock therapy to the heart aimed at terminating the detected arrhythmia. To this end, the microcontroller 260 further controls a shocking circuit 216 by way of a control signal 218. The shocking circuit 216 generates shocking pulses of low (up to 0.5 Joules), moderate (0.5–10 Joules), or high energy (11 to 40 Joules), as controlled by the microcontroller 260. Such shocking pulses are applied to the patient's heart 212 through at least two shocking electrodes, and as shown in this embodiment, selected from the left atrial coil electrode 228, the RV coil electrode 236, and/or the SVC coil electrode 238. As noted above, the housing 240 may act as an active electrode in combination with the RV electrode 236, or as part of a split electrical vector using the SVC coil electrode 238 or the left atrial coil electrode 228 (i.e., using the RV electrode as a common electrode).

The above described pacing device 110 was described as an exemplary pacing device. One or ordinary skill in the art would understand that embodiments of the present invention can be used with alternative types of pacing devices. Accordingly, embodiments of the present invention should not be limited to use only with the above described device.

Maintaining a High Percentage of Bi-Ventricular Pacing

As mentioned above, bi-ventricular (BiV) pacing is often used in patients with heart failure (HF) and ventricular desynchrony to deliver cardiac resynchronization therapy (CRT), which is designed to reduce symptoms by restoring a more appropriate sequence of ventricular contraction. Normal Bi-V pacing includes pacing or sensing in the right atrium, then (after a programmed time period) pacing in ventricles. In this manner, the BiV pacing tracks the rate of the atria (where the heart beat starts).

In employing CRT as a treatment for HF, the CRT device of a preferred embodiment of the invention is ideally trying to pace the left and right ventricles all (i.e., 100%) of the time, to restore the mechanical synchrony that the patient's intrinsic (i.e., non-paced) ventricular activity does not provide. When a patient who is being BiV paced goes into AF, which is a fast, disorganized rhythm in the atrium, the atrial tracking function of the pacemaker is such that the pacemaker may sense the atrial fibrillation irregularly, and, therefore, pace the ventricles fast (up to the maximum allowable pacing rate) and irregularly. At other times, the disorganized rhythm may be conducted to the ventricles at a fast, often irregular, rate (though not as fast as the atrial rate); if that rate is faster than the minimum rate the pacemaker is set to maintain, the ventricles may not be paced. The former instance (irregular tracking of the atrial fibrillation) can create a clinical problem, in that the pacemaker may be pacing the ventricles faster than is physiologically appropriate, and often irregularly; this can cause patient symptoms and/or exacerbation of the patient's heart failure. This situation is, as previously described, dealt with in current pacemakers by having the pacemaker switch from its atrial tracking mode to a non-atrial tracking mode; this behavior is referred to as mode switch. In the non-atrial tracking mode, the ventricular pacing rate is decoupled from the inappropriately fast, irregular atrial rate, and is maintained at a more appropriate level. However, even when a mode switch occurs, if the patient's conducted rate is faster than the designated pacing rate, ventricular pacing will be partially or completely inhibited. This is less than ideal for a patient with a CRT device, since appropriate resynchronization of the ventricles can only be maintained by pacing.

Accordingly, in the face of AF that gets rapidly conducted into the ventricles, there is a need to maintain a high percentage of BiV pacing, in order to keep the ventricles synchronized. This percentage can be defined as: BiV paced beats/(BiV paced beats + intrinsic ventricular beats). It is noted that the terms "synchronized" and "synchrony" refer to the left and right ventricles contracting at substantially the same time, or at a selected offset from one another. In contrast, the terms "desynchronized" and "desynchrony" refer to the left and right ventricles contracting in a disorganized manner, i.e., not consistently at substantially the same time, or not at a selected offset.

Embodiments of the present invention described herein are designed to adjust the pacing rate during mode switch in such a way as to increase and hopefully maximize BiV pacing to the extent possible. The term mode switch, as used herein, is used to refer to the state of a pacemaker that in a non-atrial tracking mode (as opposed to an atrial tracking mode).

For pacemakers designed to operate in mode switch, there is typically a programmed mode switch base rate (MSBR) that specifies the minimum rate at which the ventricles should be paced during mode switch (e.g., MSBR=80 ppm). In some devices, the MSBR may be fixed at a particular value; in other, rate responsive devices, the MSBR may be adjusted between a minimum and maximum value according to the input received from a sensor (e.g., an activity sensor). However, when the patient's intrinsic conduction (because of an atrial tachyarrhythmia) is faster than the programmed MSBR, the pacemaker will be inhibited. Inhibition, as referred to herein, is a pacemaker response in which an output pulse is suppressed, i.e., inhibited, when an intrinsic event is sensed during the alert interval. In normal demand type pacing, inhibition is not a problem. However, with BiV pacing for HF patients or other CRT patients, where the goal is to purposely pace the ventricles in order to keep them synchronized, inhibition of the pacemaker is a problem. Embodiments of the present invention overcome the inhibition problem by pacing the ventricles at a rate that is fast enough that it overrides the patient's intrinsic conduction rate during an atrial tachyarrhythmia.

More specifically, embodiments of the present invention adjust the MSBR such that when the pacemaker is in mode switch (i.e., in a non-atrial tracking mode), the MSBR is kept high enough that BiV pacing generally occurs at least a minimum acceptable amount, referred to as the minimum acceptable pacing criterion (MAPC). This MAPC could be defined, e.g., as a pacing percentage or as an X out of Y criterion. For example, a MAPC can specify that 90% of all ventricular beats should be paced, or that 9 out of 10 ventricular beats should be paced.

Figure 3:
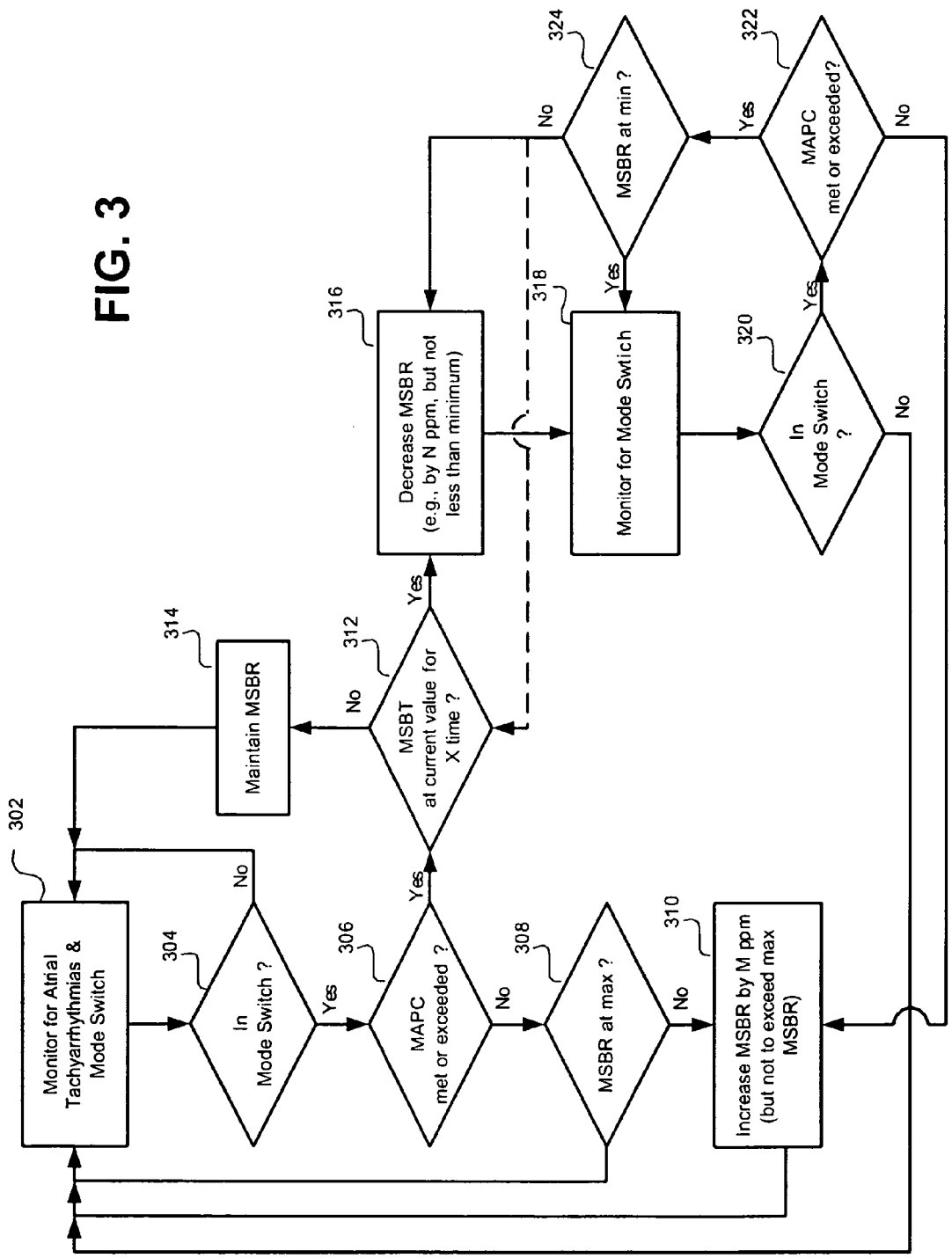
FIG. 3 is a high level flow diagram useful for describing embodiments of the present invention.

The high level flow diagram of FIG. 3 will now be used to explain specific implementations of the present invention. As indicated at step 302, a pacemaker monitors for atrial tachyarrhythmias (e.g., atrial fibrillation) and, when a tachyarrhythmia is sensed that meets the device's mode switch detection criteria, a mode switch will occur. Such a pacemaker will have a specified MAPC, minimum MSBR, maximum MSBR and initial MSBR (which can be anywhere between and inclusive of the minimum and maximum MSBRs). Each of these could be fixed or physician-programmable. This and other steps can be performed, e.g., by a controller (e.g., 260) of the pacemaker.

At step 304, there is a determination of whether the pacemaker is in mode switch (i.e., in a non-atrial tracking mode). If the pacemaker is not in mode switch (i.e., if the device is in an atrial tracking mode), then flow goes back to step 302. However, if the pacemaker is in mode switch (i.e., if the device has switched from an atrial tracking to non-atrial tracking mode), then flow goes to step 306.

At step 306 there is a determination of whether the minimum acceptable pacing criterion (MAPC) is satisfied (i.e., met or exceeded). As mentioned above, the MAPC, which defines the minimum amount of BiV pacing (as compared to intrinsic ventricular beating) that is considered acceptable, can be specified as a pacing percentage or as an X out of Y criterion. If the MAPC is not met or exceeded, then flow goes to step 308, where there is a determination of whether the MSBR is at its maximum. If the MSBR is at its maximum, then flow returns to step 302, because it cannot be increased any further. However, if the MSBR is not at its maximum, then flow goes to step 310 where the MSBR is increased (in an attempt to increase the MSBR above the intrinsic rate of the ventricles so that the MAPC can be met). In accordance with one embodiment, the increase at step 310 is by a fixed amount, e.g., by M pulses per minute (ppm). In another embodiment, the increased at step 310 is by a percentage (e.g., 2%). In still another embodiment, the increase of the MSBR at step 310 can be accomplished by a reduction in the intervals between beats (e.g., by reducing the interval between consecutive beats by N msec). Either way, the increased MSBR should not exceed the maximum MSBR. After the increase in MSBR at step 310, flow returns to step 302.

Returning to step 306, if the MAPC is met or exceed, then flow will go to step 312. At step 312, there is a determination of whether the MSBR has been at its current value for at least a specified period of time (e.g., X minutes). If it has not, the MSBR is maintained at its current value, as indicated at step 314, and then flow returns to step 302. If the MSBR has been at its current value for at least the specified predetermined period of time (e.g., X minutes), then flow goes to step 316, where the MSBR is decreased. The decrease at step 316 can be, e.g., by a fixed amount, by a percentage, or by an increase in the interval between beats. Such a decrease increment can be the same as, or different than, the increase increment used at step 310. The MSBR should not be decreased such that it is less than the minimum MSBR. After the decrease in MSBR at step 316, flow goes to step 318.

At step 318 the pacemaker monitors for mode switch, so that there can be a determination at step 320 whether the device is still in mode switch (i.e., whether the device is still pacing in a non-atrial tracking mode). If the pacemaker is no longer in mode switch (i.e., if the device has changed back to an atrial tracking mode), then flow returns to step 302. If the pacemaker is still in mode switch, then flow goes to step 322, where there is another determination of whether the MAPC is met or exceeded. If the MAPC is no longer met or exceeded, then flow goes to step 310, where the MSBR is increased (in an attempt to satisfy the MAPC, as was explained above). If it is determined at step 322 that the MAPC is still met or exceeded, then flow goes to step 324, where there is a determination of whether the minimum MSBR has been reached. If the minimum MSBR has not been reached, then flow returns to step 316, where the MSBR is again decreased (as was explained above). Alternatively, if it is determined at step 324 that the MSBR has not been reached, flow can return to step 312, thereby slowing down the rate at which the MSBR is further decreased (if appropriate).

If it is determined at step 316 that the minimum MSBR has been reached, then flow returns to step 318 and then step 320, which were just discussed. In this manner, the MSBR can be maintained at the minimum MSBR until the MAPC is no longer satisfied, at which point the MSBR will be increased, or until the patient's atrial arrhythmia stops and the mode switch is terminated (and the pacemaker returns to an atrial tracking mode).

In summary, when the pacemaker switches from an atrial tracking mode to a non-atrial tracking mode in response to an atrial fibrillation (or other atrial tachyarrhythmias) being detected, the device paces at the MSBR, which can be an initial rate or a rate that has been specified by the algorithm of FIG. 3 (but kept between a minimum and a maximum MSBR). While in mode switch, the device keeps determining whether the MAPC is being satisfied (i.e., met or exceeded). If the frequency of BiV pacing does not satisfy the MAPC, then the pacemaker will gradually increase the MSBR (but only up to the maximum MSBR) until the MAPC is satisfied, as specified in steps 304 through 310. When the frequency of BiV pacing satisfies the MAPC, then the pacemaker will periodically (e.g., after a time based period or an elapsed interval criterion) decrease the MSBR until either the minimum MSBR is reached or the MAPC is no longer satisfied, as specified in steps 316 through 324.

Because the BiV pacing and/or various physiologic factors could ultimately slow the patient's intrinsic AV conduction, even after the MSBR is increased, the pacemaker will periodically (e.g., after a time-based period or an elapsed interval criterion) attempt to decrease the MSBR until either the minimum MSBR is reached or the MAPC is no longer satisfied. When the minimum MSBR is reach, the pacemaker maintains pacing at the minimum MSBR until the MAPC is no longer satisfied, or until the patient's atrial arrhythmia stops and the mode switch is terminated. When the MSBR is no longer satisfied (either because it was decreased too low or the intrinsic conduction increased), the MSBR is increased until the MAPC is again satisfied. In this fashion, the patient's pacing rate (defined by the MSBR) is maintained at about the minimum rate that allows maintenance of the desired degree of pacing (as defined by the MAPC).

It is noted that the term periodically is not meant to imply that the periods of time (i.e., intervals) between successive events are exactly the same. Rather, the term periodically is meant to imply that an event occurs multiple times, wherein the interval between each time may or may not be equal. For example, a periodic event may only occur when a specific temporal condition is satisfied (e.g., there has been no change in the MSBR for at least 1 minute).

The present invention has been described above with the aid of functional building blocks illustrating the performance of specified functions and relationships thereof. The boundaries of these functional building blocks have often been arbitrarily defined herein for the convenience of the description. Alternate boundaries can be defined so long as the specified functions and relationships thereof are appropriately performed. Any such alternate boundaries are thus within the scope and spirit of the claimed invention. For example, it would be possible to combine or separate some of the steps shown in FIG. 3. Further, it is possible to change the order of some of the steps shown in FIG. 3, without substantially changing the overall events and results.

The previous description of the preferred embodiments is provided to enable any person skilled in the art to make or use the embodiments of the present invention. While the invention has been particularly shown and described with reference to preferred embodiments thereof, it will be understood by those skilled in the art that various changes in form and details may be made therein without departing from the spirit and scope of the invention.

What is claimed is:

1. A method for maintaining a high percentage of bi-ventricular pacing after a pacing device switches from an atrial tracking bi-ventricular pacing mode to a non-atrial tracking bi-ventricular pacing mode, wherein the ventricles are paced in accordance with a mode switch base rate (MSBR) during the non-atrial tracking ventricular pacing mode, the method comprising:
monitoring whether or not pacing in according with the MSBR satisfies a minimum acceptable pacing criterion (MAPC);
increasing the MSBR and pacing in accordance with the increased MSBR, when the MAPC is not satisfied; and
decreasing the MSBR and pacing in accordance with the decreased MSBR, when the MAPC is satisfied.

2. The method of claim 1, further comprising:
monitoring how long the MSBR has been at its current value; and
wherein the decreasing the MSBR is only performed when both the MAPC is satisfied and the MSBR has been at its current value for at least a specific period of time.

3. The method of claim 2, further comprising maintaining the MSBR at its current value when the MAPC is satisfied, but for less than the specific period of time, and continuing pacing in accordance with the maintained MSBR.

4. The method of claim 1, wherein the step of increasing the MSBR when the MAPC is not satisfied includes increasing the MSBR by a fixed amount, but not allowing the MSBR to exceed a maximum MSBR.

5. The method of claim 1, wherein the step of increasing the MSBR when the MAPC is not satisfied includes increasing the MSBR by a percentage, but not allowing the MSBR to exceed a maximum MSBR.

6. The method of claim 1, wherein the step of increasing the MSBR when the MAPC is not satisfied includes decreasing an amount of time between successive pacing pulses, but not allowing the MSBR to exceed a maximum MSBR.

7. The method of claim 1, wherein the step of decreasing the MSBR when the MAPC is satisfied includes decreasing the MSBR by a fixed amount, but not allowing the MSBR to be less than a minimum MSBR.

8. The method of claim 1, wherein the step of decreasing the MSBR when the MAPC is satisfied includes decreasing the MSBR by a percentage, but not allowing the MSBR to be less than a minimum MSBR.

9. The method of claim 1, wherein the step of decreasing the MSBR when the MAPC is satisfied includes increasing an amount of time between successive pacing pulses, but not allowing the MSBR to be less than a minimum MSBR.

10. The method of claim 1, wherein the MAPC is defined as a percentage.

11. The method of claim 1, wherein the MAPC is defined as an N out of M criterion, where N represents a number of paced bi-ventricular contractions out of M paced plus intrinsic bi-ventricular contractions.

12. The method of claim 1, wherein a first time the pacing device switches from an atrial tracking ventricular pacing mode to a non-atrial tracking ventricular pacing mode, bi-ventricular pacing is performed in accordance with an initial MSBR.

13. The method of claim 12, wherein each further time the pacing device switches from an atrial tracking ventricular pacing mode to a non-atrial tracking ventricular pacing mode, bi-ventricular pacing occurs in accordance with a most recently used MSBR.

14. The method of claim 1, wherein the MSBR defines the rate at which to perform bi-ventricular pacing of the ventricles during the non-atrial tracking bi-ventricular pacing mode.

15. A pacing device that maintains a high percentage of bi-ventricular pacing after the pacing device switches from an atrial tracking bi-ventricular pacing mode to a non-atrial tracking bi-ventricular pacing mode, wherein the ventricles are paced in accordance with a mode switch base rate (MSBR) during the non-atrial tracking bi-ventricular pacing mode, the pacing device comprising:
a controller to monitor whether or not pacing in according with the MSBR satisfies a minimum acceptable pacing criterion (MAPC), wherein the controller increases the MSBR when the MAPC is not satisfied, and wherein the controller decreases the MSBR when the MAPC is satisfied; and
a ventricular pulse generator to generate bi-ventricular pacing pulses for delivery to the ventricles;
wherein the controller causes the ventricular pulse generator to generate bi-ventricular pacing pulses in accordance with the MSBR during the non-atrial tracking bi-ventricular pacing mode.

16. The device of claim 15, wherein the controller monitors how long the MSBR has been at its current value, and wherein the controller only decreases the MSBR when both the MAPC is satisfied and the MSBR has been at its current value for at least a specific period of time.

17. The device of claim 16, wherein the controller maintains the MSBR at its current value when the MAPC is satisfied, but for less than the specific period of time, and the controller causes the ventricular pulse generator to deliver bi-ventricular pacing pulses in accordance with the maintained MSBR.

18. The device of claim 15, wherein the controller increases the MSBR by a fixed amount when the MAPC is not satisfied, but does not allow the MSBR to exceed a maximum MSBR.

19. The device of claim 15, wherein the controller of increases the MSBR by a percentage when the MAPC is not satisfied, but does not allow the MSBR to exceed a maximum MSBR.

20. The device of claim 15, wherein the controller increases the MSBR when the MAPC is not satisfied, by decreasing an amount of time between successive pacing pulses, but does not allow the MSBR to exceed a maximum MSBR.

21. The device of claim 15, wherein the controller decreases the MSBR when the MAPC is satisfied, by decreasing the MSBR by a fixed amount, but does not allow the MSBR to be less than a minimum MSBR.

22. The device of claim 15, wherein the controller of decreases the MSBR when the MAPC is satisfied, by decreasing the MSBR by a percentage, but does not allow the MSBR to be less than a minimum MSBR.

23. The device of claim 15, wherein the controller decreases the MSBR when the MAPC is satisfied, by increasing an amount of time between successive pacing pulses, but does not allow the MSBR to be less than a minimum MSBR.

24. The device of claim 15, wherein the MAPC is defined as a percentage.

25. The device of claim 15, wherein the MAPC is defined as an N out of M criterion, where N represents a number of paced bi-ventricular contractions out of M paced plus intrinsic bi-ventricular contractions.

26. The device of claim 15, wherein a first time the device switches from an atrial tracking ventricular pacing mode to a non-atrial tracking ventricular pacing mode, the controller causes the ventricular pulse generator to generate bi-ventricular pacing pulse in accordance with an initial MSBR.

27. The device of claim 26, wherein each further time a mode switch occurs, from an atrial tracking ventricular pacing mode to a non-atrial tracking ventricular pacing mode, the controller causes the ventricular pulse generator to generate bi-ventricular pacing pulse in accordance with a most recently used MSBR.

28. The device of claim 15, wherein the MSBR defines the rate at which to perform bi-ventricular pacing of the ventricles during the non-atrial tracking ventricular pacing mode.

29. A pacing device that maintains a high percentage of bi-ventricular pacing after the device switches from an atrial tracking bi-ventricular pacing mode to a non-atrial tracking bi-ventricular pacing mode, wherein the ventricles are paced in accordance with a mode switch base rate (MSBR) during the non-atrial tracking ventricular pacing mode, the device comprising:
 monitoring means for monitoring whether or not bi-ventricular pacing in according with the MSBR satisfies a minimum acceptable pacing criterion (MAPC);
 adjusting means for adjusting the MSBR, wherein the adjusting means increases the MSBR when the MAPC is not satisfied, and wherein the adjusting means decreases the MSBR when the MAPC is satisfied; and
 pacing means for pacing in the ventricles in accordance with the MSBR.

30. The system of claim 29, further comprising:
 a means for monitoring how long the MSBR has been at its current value; and
 wherein the adjusting means only decreases the MSBR when the MAPC is satisfied and the MSBR has been at its current value for at least a specific period of time.

31. A method for maintaining a high percentage of bi-ventricular pacing during a non-atrial tracking bi-ventricular pacing mode, wherein the ventricles are paced in accordance with a mode switch base rate (MSBR) during the non-atrial tracking bi-ventricular pacing mode, the method comprising:
 monitoring whether or not pacing in according with the MSBR satisfies a minimum acceptable pacing criterion (MAPC); and
 when the MAPC is not satisfied, incrementally increasing the MSBR until the MAPC is satisfied or a maximum MSBR is reached; and
 when the MAPC is satisfied, incrementally decreasing the MSBR until the MAPC is no longer satisfied or a minimum MSBR is reached.

32. The method of claim 31, further comprising:
 monitoring how long the MSBR has been at its current value; and
 wherein the incrementally decreasing the MSBR is only performed when both the MSBR is satisfied and the MSBR has been at its current value for at least a specific period of time.

33. A method for maintaining a high percentage of bi-ventricular pacing during a non-atrial tracking bi-ventricular pacing mode, wherein the ventricles are paced in accordance with a mode switch base rate (MSBR) during the non-atrial tracking bi-ventricular pacing mode, the method comprising:
 monitoring whether or not pacing in according with the MSBR satisfies a minimum acceptable pacing criterion (MAPC); and
 when the MAPC is not satisfied, gradually increasing the MSBR until the MAPC is satisfied or a maximum MSBR is reached; and
 when the MAPC is satisfied, gradually decreasing the MSBR until the MAPC is no longer satisfied or a minimum MSBR is reached.

34. The method of claim 33, further comprising:
 monitoring how long the MSBR has been at its current value; and
 wherein the decreasing the MSBR is only performed when both the MSBR is satisfied and the MSBR has been at its current value for at least a specific period of time.

35. A method for maintaining a high percentage of pacing after a switch occurs from an atrial tracking ventricular pacing mode to a non-atrial tracking ventricular pacing mode, the method comprising:
 determining whether or not a minimum acceptable pacing criterion (MAPC) is satisfied; and
 if the MAPC is not satisfied, gradually increasing a mode switch base rate (MSBR) until the MAPC is satisfied or a maximum MSBR is reached.

36. The method of claim 35, wherein the MSBR defines the rate at which to perform bi-ventricular pacing of the ventricles during the non-atrial tracking ventricular pacing mode.

37. The method of claim 35, further comprising:
 if the MAPC is satisfied for at least a specified period of time, gradually decreasing the MSBR until the MAPC is no longer satisfied or a minimum MSBR is reached.

38. A method for performing bi-ventricular pacing in the face of a rapidly conducting tachyarrhythmia, comprising:
 in response to detecting an atrial tachyarrhythmia resulting in a mode switch from an atrial tracking bi-ventricular pacing mode to a non-atrial tracking bi-ventricular pacing mode, adjusting a mode switch base rate to satisfy a minimum acceptable pacing criterion.

* * * * *